(12) United States Patent
Granstam et al.

(10) Patent No.: US 9,366,665 B1
(45) Date of Patent: Jun. 14, 2016

(54) BREATH ANALYZER DEVICE

(71) Applicant: Autoliv Development AB, Vårgårda (SE)

(72) Inventors: Mathias Granstam, Västerås (SE); Bertil Hök, Västerås (SE)

(73) Assignee: AUTOLIV DEVELOPMENT AB, Vargarda (SE)

( * ) Notice: Subject to any disclaimer, the term of this patent is extended or adjusted under 35 U.S.C. 154(b) by 0 days.

(21) Appl. No.: 14/946,867

(22) Filed: Nov. 20, 2015

(30) Foreign Application Priority Data

Nov. 20, 2014 (GB) .................................. 1420647.8

(51) Int. Cl.
| | | |
|---|---|---|
| *G01N 33/48* | (2006.01) | |
| *G01N 33/497* | (2006.01) | |
| *G01N 33/98* | (2006.01) | |
| *G01N 1/22* | (2006.01) | |
| *A61B 5/097* | (2006.01) | |
| *A61B 5/08* | (2006.01) | |

(52) U.S. Cl.
CPC ............ *G01N 33/4972* (2013.01); *G01N 33/98* (2013.01); *A61B 5/082* (2013.01); *A61B 5/097* (2013.01); *G01N 2001/2244* (2013.01)

(58) Field of Classification Search
CPC . G01N 33/98; G01N 33/497; G01N 33/4972; G01N 2001/2244; A61B 5/082; A61B 5/097; Y10T 436/204165; Y10S 436/90
USPC ....... 73/23.3; 422/84; 436/132, 900; 600/532
See application file for complete search history.

(56) References Cited

U.S. PATENT DOCUMENTS

| | | | |
|---|---|---|---|
| 3,505,022 A | | 4/1970 | Luckey |
| 3,792,272 A | | 2/1974 | Harte et al. |
| 3,818,899 A | | 6/1974 | Venema |
| 5,282,473 A | | 2/1994 | Braig et al. |
| 5,321,972 A | * | 6/1994 | Stock ................. G01N 33/4972 422/84 |
| 5,376,555 A | | 12/1994 | Forrester et al. |
| 5,401,966 A | | 3/1995 | Gray et al. |
| 5,418,366 A | | 5/1995 | Rubin et al. |
| 5,515,859 A | | 5/1996 | Paz |
| 5,573,005 A | * | 11/1996 | Ueda ...................... A61B 5/083 422/84 |
| 5,871,509 A | | 2/1999 | Noren |
| 5,971,937 A | | 10/1999 | Ekström |

(Continued)

FOREIGN PATENT DOCUMENTS

| | | |
|---|---|---|
| DE | 42 35 328 A1 | 4/1994 |
| DE | 10 2011 106 410 B3 | 8/2012 |

(Continued)

*Primary Examiner* — Peter Macchiarolo
*Assistant Examiner* — Nathaniel Kolb
(74) *Attorney, Agent, or Firm* — Brinks Gilson & Lione

(57) ABSTRACT

A breath analyzer device (1) having an inlet region (2) and a sensor arrangement (3), wherein the inlet region (2) is configured to receive a breath sample from a test subject and direct the sample to the sensor arrangement (3), and the sensor arrangement is configured to provide a signal representative of the concentration of a volatile substance within the sample. The inlet region (2) includes a heater (20, 24) arranged between: a sample inlet port (6) which is open to atmospheric air outside the device (1); and a sample outlet port (11) which is open to the sensor arrangement (3), the heater (20, 24) extending at least part way along a tortuous flow channel (18) which extends between the inlet port (6) and the outlet port (11) for the direction of the sample to the sensor arrangement (3).

11 Claims, 2 Drawing Sheets

(56) References Cited

U.S. PATENT DOCUMENTS

| | | | |
|---|---|---|---|
| 6,150,177 A * | 11/2000 | Stock | G01N 33/4972 422/84 |
| 6,844,554 B2 | 1/2005 | Karlsson | |
| 8,088,333 B2 * | 1/2012 | Ahmad | A61B 5/083 422/50 |
| 8,176,766 B1 * | 5/2012 | Ruiz | G01N 1/2211 422/84 |
| 8,722,417 B2 * | 5/2014 | Ahmad | A61B 5/097 422/400 |
| 2003/0136600 A1 | 7/2003 | Breed | |
| 2004/0129056 A1 | 7/2004 | Hok et al. | |
| 2006/0044144 A1 | 3/2006 | Duval | |
| 2006/0133960 A1 * | 6/2006 | Ahmad | A61B 5/083 422/83 |
| 2007/0232950 A1 | 10/2007 | West | |
| 2008/0056946 A1 * | 3/2008 | Ahmad | A61B 5/097 422/68.1 |
| 2008/0061238 A1 | 3/2008 | Hok et al. | |
| 2009/0087920 A1 | 4/2009 | Pettersson et al. | |
| 2013/0231871 A1 | 9/2013 | Hök et al. | |

FOREIGN PATENT DOCUMENTS

| | | |
|---|---|---|
| EP | 0 752 584 A2 | 1/1997 |
| EP | 1 441 212 A1 | 7/2007 |
| WO | WO 2007/114751 A1 | 10/2007 |

* cited by examiner

BREATH ANALYZER DEVICE

CROSS-REFERENCE TO RELATED APPLICATIONS

This application claims priority to Great Britain Application No. 1420647.8, filed Nov. 20, 2014.

FIELD OF THE INVENTION

The present invention relates to a breath analyser device.

BACKGROUND

It is important in a number of situations to be able accurately to analyse the exhaled breath of a test subject. The most common reason for doing this is to detect the presence of alcohol in the test subject's breath, which will of course be indicative of the test subject having a raised blood-alcohol level and thus impaired judgment and reaction times. Testing for alcohol in this way is very important for safety reasons in a large number of situations including, for example, the operation of heavy or dangerous machinery, the operation of aircraft, and the operation of motor vehicles. Breath testing for alcohol is now widely used in the area of law enforcement and is routinely carried out on motor vehicle drivers on the road networks of most major countries, with strict penalties in place for drivers found to be driving under the influence of alcohol.

Alcohol is a major factor in a very large number of road accidents, and so great efforts are made to reduce the incidence of driving under the influence of alcohol. One proposal which is now being considered more widely is the provision of so-called "alco-locks" in motor vehicles which will prevent operation of the motor vehicle until an approved breath sample has been given by the driver having an alcohol content below a predetermined maximum threshold. It is envisaged that the device of the present invention will be particularly useful in such alco-lock arrangements. However, it is to be appreciated that the invention is not limited to use in alco-lock arrangements, and could find wider application in the field of alcohol breath testing. The device of the present invention could be more widely employed in breath analysis more generally, and may not even be restricted to testing for the presence of alcohol. Nevertheless, the present invention is described herein with specific reference to alcohol testing.

Whilst alcohol testing for evidentiary of diagnostic purposes is generally achieved by infrared spectroscopy which is very accurate, a simpler method of alcohol testing is normally used for screening purposes; for example at the roadside by law enforcement personnel, or in the case of alco-locks installed in vehicles. Alcohol testing for screening purposes has therefore previously been achieved via catalysis; for example using fuel cells or semiconductor devices. These types of device are advantageous in terms of production cost, but have been found to suffer from problems of unreliability. The catalytic function is difficult to control, and the sensors have a limited lifetime. Furthermore, devices of this type require a test subject to deliver forced expiration into a tight-fitting mouthpiece which can be problematic for people with impaired respiratory function, and will generally be inconvenient and off-putting for drivers in the case of vehicle alco-locks.

It has therefore been proposed to provide improved breath analyser devices that do not require physical contact between the device and the test subject. This type of device is particularly advantageous in the case of alco-locks because it can be conveniently positioned on the dashboard, steering wheel, or A-pillar of a motor vehicle for receipt of a breath sample from a driver test subject in a normal, or reasonably normal, driving position. However, testing in this manner will of course mean that the breath sample is diluted with ambient air.

US2013/0231871 A1 proposes a type of no-contact breath analyser device which address the issue of ambient air dilution of the breath sample by measuring the concentration of a tracer substance such as carbon dioxide within the sample in order to estimate the degree of dilution and thereby allow the estimation of the true breath concentration of alcohol. Whilst this type of device has some very significant benefits, it has been found that accuracy problems can occur when gas entering the device is cold. One problem which arises is that the cold gas can cause condensation to be formed inside the sensing region of the device which can disrupt the operation of the sensors inside the device. However, it has also been found that simply the low temperature of the inlet gas can also disrupt the sensors.

There is therefore a need to address these problems, which it is to be noted are not exclusive to the type of device proposed in US2013/023181 A1, and can also arise in other types of breath analyser device.

It is an object of the present invention to provide an improved breath analyser device.

SUMMARY

According to the present invention, there is provided a breath analyser device having an inlet region and a sensor arrangement, wherein the inlet region is configured to receive a breath sample from a test subject and direct the sample to the sensor arrangement, and the sensor arrangement is configured to provide a signal representative of the concentration of a volatile substance within the sample, the device being characterised in that the inlet region includes a heater arranged between: a sample inlet port which is open to atmospheric air outside the device; and a sample outlet port which is open to the sensor arrangement, the heater extending at least part way along a tortuous flow channel which extends between the inlet port and the outlet port for the direction of the sample to the sensor arrangement.

Conveniently, the heater extends along substantially the entire length of the tortuous flow channel.

The tortuous flow channel may have a spiral configuration the a serpentine configuration or a meandering configuration.

Optionally, the flow channel has an outer end and an inner end, the outer end being spaced radially outwardly from the inner end, and wherein the sample inlet port is provided in fluid communication with the outer end, and the sample outlet port is provided in fluid communication with the inner end.

Conveniently, the heater is integral with a wall defining the tortuous flow channel.

Advantageously, the wall is formed from a film of polymeric material.

Optionally, the film is provided as a length of tape which is wound upon itself to form a coil having a plurality of spaced-apart turns between which the tortuous flow channel is defined.

Advantageously, the wound tape is provided inside a housing forming at least part of the inlet region.

Conveniently, the housing has a pair of spaced-apart end-walls between which the wound tape is provided, the sample inlet port being formed as an aperture through one of the end-walls, and the sample outlet port being formed as an aperture through the other of the end-walls.

Optionally, the heater is provided in the form of one or more heating elements formed on or in the polymeric material.

Conveniently, or each heating element is provided in the form of a thin electrically resistive element connected to an electrical supply.

Preferably, the resistive element is a metal foil.

Alternatively, the resistive element may be a thin layer of silicone resin including conductive nanoparticles.

Advantageously, the sample inlet and outlet ports are each provided with a temperature sensor configured to measure the temperature of a sample breath directed through the respective port.

Optionally, the device includes a controller configured to control the heater in response to temperature readings from at least one of the temperature sensors.

Conveniently, the length/width ratio of the tortuous flow channel is at least 40.

BRIEF DESCRIPTION OF THE DRAWINGS

So that the invention may be more readily understood, and so that further features thereof may be appreciated, embodiments of the invention will now be described by way of example with reference to the accompanying drawings in which.

DETAILED DESCRIPTION

Figure 1:
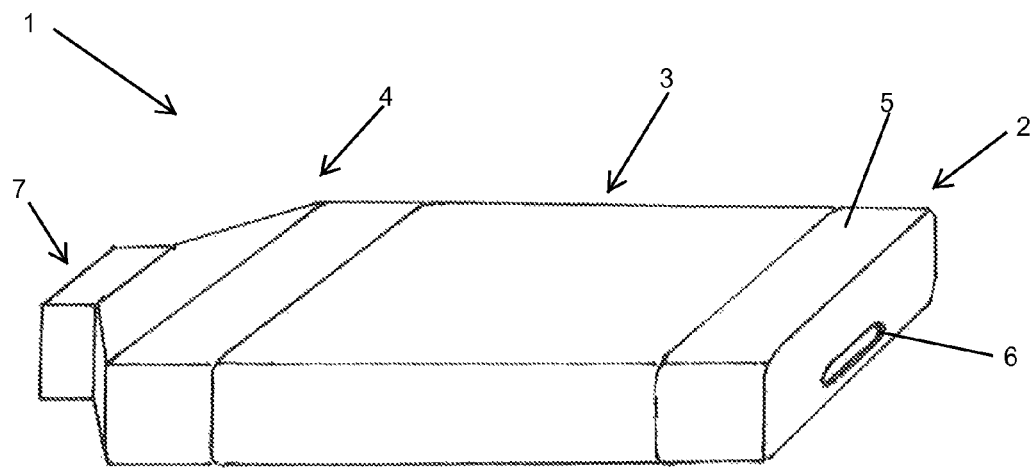
FIG. 1 is a perspective view showing an exemplary breath analyser device in accordance with the present invention.

Turning now to consider the drawings in more detail, FIG. 1 illustrates the general arrangement of a breath analyser device 1 in accordance with an embodiment of the present invention. In general terms, the device includes an inlet region 2, a sensor module 3 which incorporates a sensor arrangement, and an outlet region 4. The device 1 may be configured to operate in accordance with the principles disclosed in US2013/0231871A1, such that the sensor arrangement of the sensor module 3 may configured in a similar manner to the sensor arrangement of the device proposed therein. However, other configurations of sensor arrangement are also possible. In all embodiments it is envisaged that the sensor arrangement will be configured to provide a signal representative of the concentration of at least one volatile substance within the breath sample.

The inlet region 2 includes an inlet housing 5 having a sample inlet port 6 arranged at one end of the device 1. The inlet port 6 is open to atmospheric air outside the device 1 and is configured to receive a breath sample from a test subject. As will be explained in more detail below, the inlet region 2 of the device is configured to direct the breath sample to the sensor arrangement within the sensor module 3 of the device 1 for analysis.

The outlet region 4 of the device has an exhaust port (indicated generally at 7, but not visible in FIG. 1) at the opposite end of the device 1 to the sample inlet port 6, through which the diluted breath sample is exhausted to the atmosphere after passing through, and being analysed within, the sensor module 3. The outlet region 4 may be provided with an internal battery operated fan (not shown) to pull the gas through the device 1.

Figure 2:
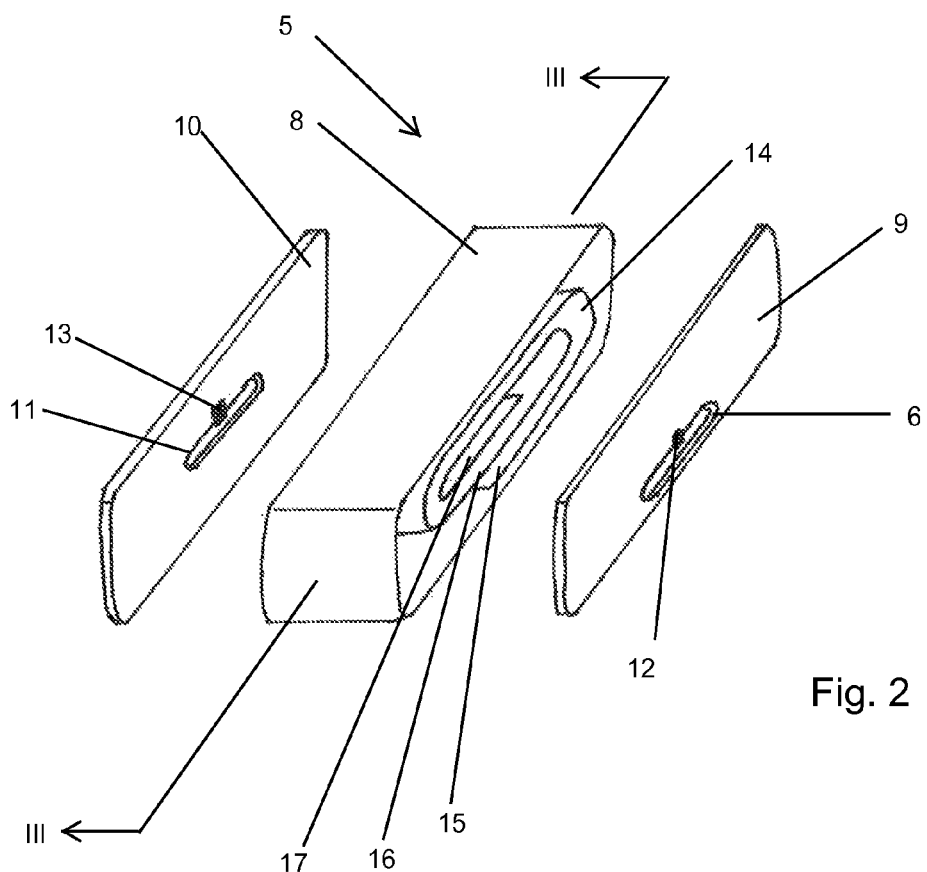
FIG. 2 is an exploded perspective view showing aspects of an inlet region of the device shown in FIG. 1.

FIG. 2 illustrates the inlet housing 5 of the inlet region in more detail, and shows the housing 5 in an exploded view. The inlet housing 5 includes three main parts, namely a peripheral sidewall 8, and opposed first and second end-walls 9, 10. Because FIG. 2 shows the housing in exploded view, it will be appreciated that the end-walls 9, 10 are shown detached from the peripheral sidewall 8. However, when fully assembled each end-wall 9, 10 will be securely and hermetically attached to the peripheral sidewall 8 around its peripheral edge to define the housing 5. It is envisaged that the peripheral sidewall 8 and the two end-walls 9, 10 will all be formed from a plastics material. The end-walls 9, 10 may thus be secured to opposite sides of the peripheral sidewall 8 by a suitable adhesive, or may be bonded thereto by other means such as via heat-fusion. When fully assembled in this manner, the inlet housing 5 will be substantially airtight except for the inlet and outlet ports 6, 11 which will represent the only openings to the housing 5.

The sample inlet port 6 is provided in the form of an aperture through the first end-wall 9. As illustrated in FIG. 2, the sample inlet port 6 is located generally centrally in the transverse direction of the device 1, and towards the bottom of the first end-wall (in the orientation illustrated), so as to be spaced only a small distance from the adjacent peripheral edge of the side-wall 9.

A sample outlet port 11, having a similar configuration to the sample inlet port 6, is provided in the form of an aperture through the second end-wall 10. The sample outlet port 11 is aligned with the sample inlet port 6 in a transverse sense, and so is also located generally centrally in the transverse direction of the device. However, in contrast to the sample inlet port 6, the sample outlet port 11 is also located centrally of the second end-wall 10 in the vertical sense (in the orientation illustrated) so that it is located in the region of the geometric center of the second end-wall 10. In the embodiment illustrated, both the sample ports 6, 11 have a generally elongate shape and may be considered to represent a somewhat long and thin oval shape.

The first end-wall 9 supports an inlet temperature sensor 12 which is arranged to protrude partially across the sample inlet aperture 6. However, in other embodiments it is envisaged that the inlet temperature sensor 12 could be provided in a slightly different position or orientation providing it is suitably located to measure the temperature of gas flowing through the sample inlet port 6. Similarly, the second end-wall supports a substantially identical outlet temperature sensor 13 which is arranged to measure the temperature of gas flowing through the sample outlet port 11. It is proposed that the temperature sensors 12, 13 will be operatively connected to an electronic controller (not shown) forming part of the device 1. The temperature sensors 12, 13 are both miniature in size and are preferably configured such that their dimensions do not exceed 2×2×4 mm, in order that the sensors will have a fast response time; typically of less than 0.5 seconds. Furthermore, it is proposed that the sensors 12, 13 will be electrically connected to the electronic controller by conductive wires which are preferably thinner than 0.1 mm in order to minimize heat conduction.

As will be appreciated having regard to FIG. 1, when the inlet housing 5 is fully assembled as part of the device 1, the second end-wall 10 will be provided in facing relation to the sensor module 3 of the device, such that the sample outlet port 11 will be arranged so as to be open towards the sensor arrangement therein, for the passage of gas towards the sensor arrangement.

There is provided an elongate length of flexible tape 14 inside the inlet housing 5, which is clearly visible in the exploded view of FIG. 2. It is proposed that the flexible tape 14 will be provided in the form of a thin film of polymeric material, and as shown in particular in FIG. 2 the tape 14 is loosely wound upon itself to form a generally spiral-shaped coil inside the peripheral sidewall 8 of the housing 5, the coil having a plurality of spaced-apart turns 15, 16, 17. When the housing 5 is closed by securing the end-walls 9, 10 to the peripheral sidewall 8, the coiled tape becomes located between the end-walls 9, 10, with its side edges engaging the innermost surfaces of the end-walls 9, 10. It is envisaged that in some embodiments the side edges of the coiled tape 14 may be bonded to respective end-walls 9, 10.

In preferred embodiments it is proposed that the flexible tape 14 will have a length of between 160 mm and 250 mm, a thickness of between 0.1 mm and 0.2 mm, and a width (i.e. as measured between the two end-walls 9, 10) of between 7 mm and 15 mm. The tape 14 is preferably wound such that the spacing between successive turns 15, 16, 17 of the coil is between 2 mm and 4 mm. The tape 14 will thus preferably have a length/turn-spacing ratio of at least 40, for reasons that will become apparent hereinafter.

Figure 3:
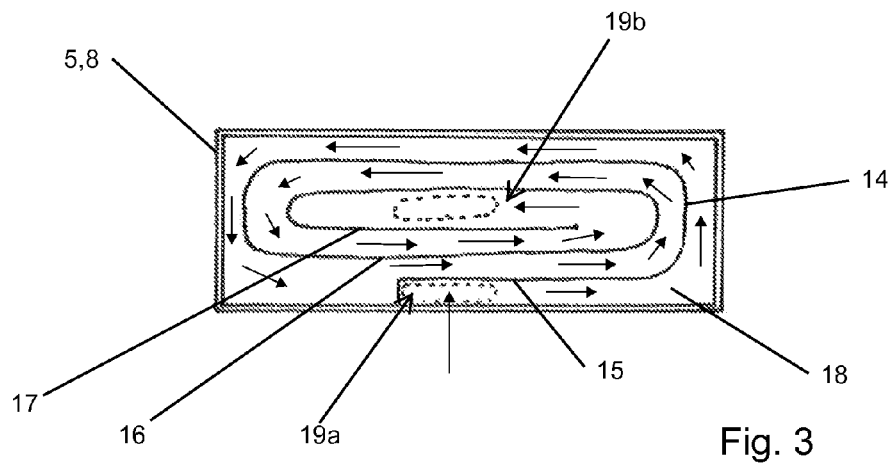
FIG. 3 is a cross-sectional view through the inlet region, as viewed along line III-III in FIG. 2.

As will therefore be appreciated, particularly with reference to FIG. 3, the space between the peripheral sidewall 8 and the outer turn 15 of the coiled tape, and the space between successive spaced-apart turns 15, 16, 17 of the tape 14 defines a flow channel 18 inside the housing 5. The tape 14 thus effectively defines a wall of the flow channel 18. As will be noted, the flow channel 18 thus has a tortuous and generally spiral configuration on account of following the spiral wind of the coiled tape 14. As will therefore be appreciated, the tortuous flow channel 18 will have a length/width ratio which at least approximately equals the length/turn-spacing ratio of the wound tape 14, and is thus preferably at least 40.

Also having regard to FIG. 3, it will be noted that the radially outer end 19a of the flow channel 18, generally adjacent the peripheral sidewall 8 of the housing 5, is positioned adjacent and thus in fluid communication with the sample inlet port 6 in the first end-wall 9 of the housing 5. Similarly the other, radially inner end 19b of the flow channel 18 is positioned adjace and thus in fluid communication with the sample outlet port 11 in the second end-wall 10 of the housing 5. As will thus be appreciated, a breath sample directed into the inlet port 6 from a test subject will be directed along the tortuous flow channel 18 inside the inlet housing 5, as illustrated by the arrows in FIG. 3, and out through the sample outlet port 11 towards the sensor arrangement of the device 1. This flow may be assisted by the aforementioned fan (not shown) in the outlet region 4 of the device 1. The wound tape 14 defining the wall of the flow channel 18 is provided with one or more integral heating elements along at least part of, and preferably substantially its entire length, as will now be described with reference to FIGS. 4 and 5 which depict two alternative configurations.

Figure 4:
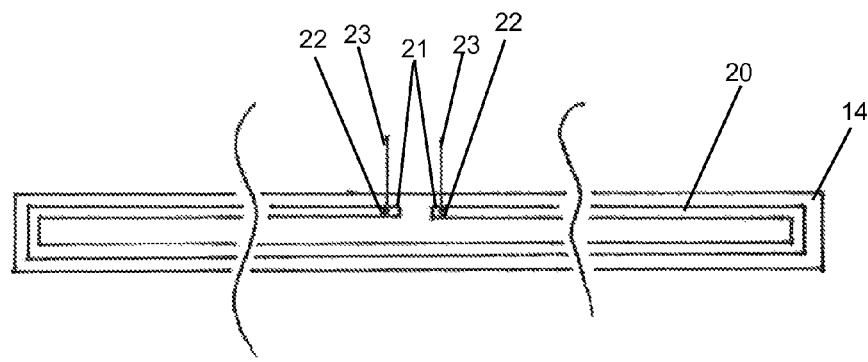
FIG. 4 shows one type of heating element forming part of the device.

FIG. 4 shows an unwound length of the polymeric tape 14, but shows the tape broken schematically at two points along its length for convenience. The tape 14 includes a flexible heating element 20 in the form of a thin metal foil having a significant electrical resistance. The heating element 20 may be bonded to the surface of the polymeric film, but may alternatively be retained within the polymeric material of the tape 14 itself. As will be noted, the heating element has a pair or spaced apart ends 21 which, in the embodiment illustrated, are located generally centrally along the length of the tape 14. It is to be appreciated, however, that in alternative embodiments the two ends 21 of the heating element 20 may be located elsewhere along the length of the tape 14. The heating element 20 extends from one of its ends 21, around substantially the entire periphery of the tape, spaced slightly inwardly of the extreme peripheral edge of the tape, and terminates at its other end 21. Each end 21 of the heating element 20 is electrically connected, for example by respective soldered joints 22, to an electrically conductive wire 23 which will be connected to a source of electrical power such as a battery, and preferably via the above-mentioned controller for the supply of DC current to the heating element 20. As will be appreciated, when the heating element 20 is energised by having an electrical current flowed through it, it will act as a resistive heater.

Figure 5:
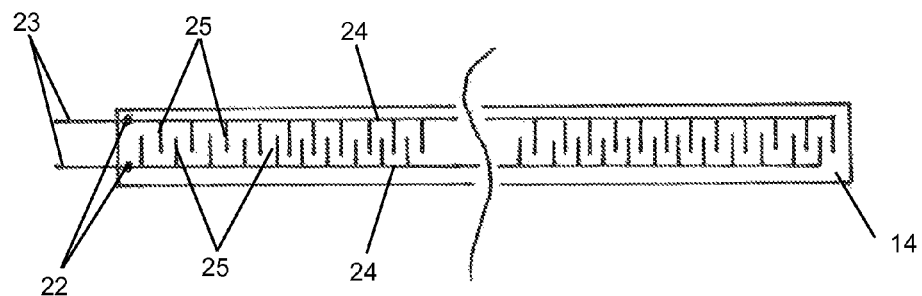
FIG. 5 shows an alternative type of heating element.

FIG. 5 shows another configuration of heating arrangement for the tape 14, and shows the tape broken schematically at a single point along its length for convenience. In this arrangement, the heater is provided by a pair of spaced-apart electrical conductors 24, each of which extends generally adjacent a respective side edge of the tape 14, and along substantially the entire length of the tape 14. The two conductors 24 may be provided in the form of a thin metal foil, such as copper or another metal with high electrical conductivity, and are spaced apart from one another along their length. Each conductor 24 has a plurality of spaced-apart fingers 25 along its length, the fingers each extending inwardly of the tape 14 in a transverse direction. As will be noted, the fingers 25 of each conductor 24 are interdigitated with those of the other conductor 24, but terminate a short distance from the opposite conductor 24. The tape 14 will include an electrical semiconductor, for example a silicone resin with conductive nanoparticles. The areas between the interdigitated fingers 25 thus constitute resistive heating elements, which preferably have a large positive temperature coefficient of resistivity. Each conductor 24 is electrically connected, for example via soldered joints 22 to a respective electrically conductive wire 23, the wires again being connected to a source of electrical power such as a battery and preferably via the controller. The source of electrical power preferably has a constant voltage such that the temperature of the heating elements represented by the spaces between the interdigitated fingers will be self-controlling, thereby minimizing the risk of the heating arrangement overheating.

As will be appreciated, when the heating elements 20, 24 are electrically energised, for example under the control of the above-mentioned controller, they will conduct or radiate heat, thereby warming the flow of air directed into the sample inlet port 6 of the device from a test subject as the sample breath is directed along the tortuous flow passage 18. In preferred embodiments in which the heating element(s) extend substantially the entire length of the wound tape 14, and thus also the substantially the entire length of the flow passage 18, the breath sample will be warmed in this manner throughout its movement through the flow passage 18, prior to its direction through the sample outlet port 11 of the device 1 and then through the sensor module 3, where it will be analysed for the presence of volatile substances. This type of heating arrangement within the inlet region 2 of the device thus serves to ensure that the air flowing through the device is sufficiently warmed so as to prevent the formation of condensation within the device, and that the sensor module 3 may operate with a breath sample at a well-defined temperature regardless of ambient temperature variations outside the device. As mentioned above, the preferred configuration of wound tape 14 used to define the flow channel 18 has a length/width ratio of at least 40. It has been found that this helps ensure adequate heat transfer from the heating element(s) 20, 24 to the air flowing through the flow passage 18.

It has been found that the optimum temperature for a breath sample as it passes through the sample outlet port 11 for subsequent passage through the sensor arrangement is at least 40° C. It is therefore proposed that the above-described controller may be configured so as to control the heating element(s) such that they will heat a breath sample appropriately for its temperature at the sample outlet port 11, as measured by the outlet temperature sensor 13, to be at least 40° C. The controller may thus be configured to regulate the heating element(s) in response to temperature readings from the inlet and outlet temperature sensors 12, 13. Additionally, it is proposed that the signal received by the controller from the inlet temperature sensor 12 may be used to indicate the presence of a breath sample, noting that the temperature detected by the inlet sensor 12 will rise slightly upon receipt of a breath sample given that exhaled breath will generally have a higher temperature than ambient air. With the heating arrangement of FIG. 5 using a constant voltage supply, the temperature will be self-controlled.

The heating arrangement of the present invention has been found to be particularly effective and efficient at heating a sample breath directed into the device 1. This is at least partly due to the manner in which the arrangement directs the breath sample along a relatively long and narrow flow passage 18 within the inlet region 2 of the device, whilst heating the sample as it passes along the passage. Because the passage 18 is narrow, only a relatively small mass of gas needs to be heated per unit length of the flow passage. Because the flow passage 18 is tortuous, it can have sufficient length within the relatively small size of the inlet region 2 to achieve a sufficient heating effect, thereby permitting the device 1 to relatively compact.

Whilst the invention has been described above with specific reference to an embodiment in which the tortuous flow channel 18 has a generally spiral configuration, it is to be noted that other flow channel configurations are also possible. For example, the tortuous flow channel 18 could take a serpentine or otherwise meandering configuration.

Furthermore, other embodiments of the invention may be configured such that the inlet housing 5 may include two or more tortuous flow channels 18 arranged to accept and direct a sample breath in a cascade manner, thereby further increasing the length/width of the complete flow channel arrangement and further improving heat transfer from the heating elements 20, 24 to the air flow through the channel.

While the above description constitutes the preferred embodiment of the present invention, it will be appreciated that the invention is susceptible to modification, variation and change without departing from the proper scope and fair meaning of the accompanying claims.

The invention claimed is:

1. A breath analyzer device configured to receive a breath sample from a test subject and direct the sample to a sensor arrangement, the sensor arrangement of a type configured to provide a signal representative of the concentration of a volatile substance within the sample, the breath analyzer device comprising an inlet region that includes a heater arranged between: a sample inlet port which is open to atmospheric air outside the device; and a sample outlet port, which is open to the sensor arrangement, the heater extending at least part way along a tortuous flow channel which extends between the inlet port and the outlet port for the direction of the sample to the sensor arrangement; wherein the heater is integral with a wall defining the tortuous flow channel; wherein the wall is provided as a length of tape which is wound upon itself to form a coil having a plurality of spaced-apart turns between which the tortuous flow channel is defined; wherein the wound tape is provided inside a housing forming at least part of the inlet region; wherein the housing has a pair of spaced-apart end-walls between which the wound tape is provided, the sample inlet port being formed as an aperture through one of the end-walls, and the sample outlet port being formed as an aperture through the other of the end-walls.

2. The device according to claim 1, wherein the heater extends along substantially the entire length of the tortuous flow channel.

3. The device according to claim 1, wherein the flow channel has an outer end and an inner end, the outer end being spaced radially outwardly from the inner end, and wherein the sample inlet port is provided in fluid communication with the outer end, and the sample outlet port is provided in fluid communication with the inner end.

4. The device according to claim 1, wherein the wall is formed from a film of polymeric material.

5. The device according to claim 4, wherein the heater is provided in the form of one or more heating elements formed on or in the polymeric material.

6. The device according to claim 5, wherein the or each heating element is provided in the form of a thin electrically resistive element connected to an electrical supply.

7. The device according to claim 6, wherein the resistive element is a metal foil.

8. A device according to claim 6, wherein the resistive element is a thin layer of silicone resin including conductive nanoparticles.

9. The device according to claim 1, wherein the sample inlet and outlet ports are each provided with a temperature sensor configured to measure the temperature of a sample breath directed through the respective port.

10. The device according to claim 9, further comprising a controller configured to control the heater in response to temperature readings from at least one of the temperature sensors.

11. The device according to claim 1, wherein the length/width ratio of the tortuous flow channel is at least 40.

* * * * *